(12) United States Patent
Boschetti et al.

(10) Patent No.: US 8,410,796 B2
(45) Date of Patent: Apr. 2, 2013

(54) METHOD FOR CALIBRATING APPARATUSES FOR DETERMINING THE MOISTURE CONTENT OF PRODUCTS BASED ON CAPACITIVE MEASUREMENTS, AND DEVICE FOR STIMULATING THE DIELECTRIC PROPERTIES OF PRODUCTS, SUCH AS WOOD, FOR USE IN THIS METHOD

(75) Inventors: Marco Boschetti, Trento (IT); Andrea Gottardo, Bressanone (IT)

(73) Assignee: Microtec S.R.L., Bressanone (IT)

( * ) Notice: Subject to any disclaimer, the term of this patent is extended or adjusted under 35 U.S.C. 154(b) by 368 days.

(21) Appl. No.: 12/720,267

(22) Filed: Mar. 9, 2010

(65) Prior Publication Data

US 2010/0231231 A1 Sep. 16, 2010

(30) Foreign Application Priority Data

Mar. 10, 2009 (IT) .............................. VR2009A0028

(51) Int. Cl.
*G01R 27/26* (2006.01)
(52) U.S. Cl. ......... 324/664; 324/601; 324/663; 324/670
(58) Field of Classification Search .................. 324/601, 324/663–670
See application file for complete search history.

(56) References Cited

U.S. PATENT DOCUMENTS

| | | | | |
|---|---|---|---|---|
| 2,076,441 A * | 4/1937 | Berry | ............................ | 324/667 |
| 3,012,193 A * | 12/1961 | Breen | ............................ | 324/668 |
| 3,241,062 A * | 3/1966 | Baird | ............................ | 324/665 |
| 3,253,458 A * | 5/1966 | Katz et al. | ............................ | 73/73 |
| 3,290,588 A * | 12/1966 | Norwich | ............................ | 324/667 |
| 3,311,823 A | 3/1967 | Benson, Jr. | | |
| 3,323,046 A * | 5/1967 | Liu | ............................ | 324/666 |
| 3,339,137 A * | 8/1967 | Perry | ............................ | 324/689 |
| 3,430,140 A * | 2/1969 | West et al. | ............................ | 324/666 |
| 3,504,280 A * | 3/1970 | Byrd | ............................ | 324/667 |
| 3,593,128 A * | 7/1971 | Perry | ............................ | 324/666 |
| 3,646,434 A * | 2/1972 | Norwich | ............................ | 324/669 |
| 3,794,911 A * | 2/1974 | Fathauer | ............................ | 324/668 |
| 4,066,951 A | 1/1978 | Wang | | |
| 4,147,976 A * | 4/1979 | Wang | ............................ | 324/689 |
| 4,433,286 A * | 2/1984 | Capots | ............................ | 324/663 |
| 4,540,936 A * | 9/1985 | Walsh | ............................ | 324/690 |

(Continued)

FOREIGN PATENT DOCUMENTS

| | | |
|---|---|---|
| GB | 507181 A | 7/1938 |
| WO | 2006/102083 A2 | 9/2006 |

*Primary Examiner* — Huy Q Phan
*Assistant Examiner* — Temilade S Rhodes-Vivour
(74) *Attorney, Agent, or Firm* — Pearne & Gordon LLP

(57) ABSTRACT

A method for calibrating apparatuses for determining the moisture content of products based on capacitive measurements comprises the following operating steps:
   Inserting a device (1) for simulating the dielectric properties of products in a measuring area of an apparatus (2) to be calibrated;
   taking a capacitive measurement with the apparatus (2) while the device (1) is inserted in the measuring area;
   modifying the device (1) settings at least once and taking the capacitive measurement again, for each different setting value;
   comparing each capacitive measurement taken this way with a corresponding known reference capacitive measurement;
   calibrating the apparatus (2) based on this comparison.
In turn, the device used in the method comprises at least a first receiving antenna (3), at least an electric terminal (4), in practice electrically connectable to the apparatus (2), and at least one adjustable impedance (5) for modifying the settings of the device (1), and which is electrically connected between the first antenna (3) and the electric terminal (4).

16 Claims, 4 Drawing Sheets

U.S. PATENT DOCUMENTS

| | | |
|---|---|---|
| 4,924,173 A | 5/1990 | Dishman |
| 5,521,515 A * | 5/1996 | Campbell .................... 324/674 |
| 6,147,503 A | 11/2000 | Nelson et al. |
| 6,388,453 B1 | 5/2002 | Greer |
| 6,784,671 B2 | 8/2004 | Steele et al. |
| 7,068,050 B2 | 6/2006 | Steele et al. |
| 2005/0279855 A1 * | 12/2005 | Baker et al. .................... 239/71 |
| 2006/0261822 A1 | 11/2006 | Fraser et al. |
| 2008/0164887 A1 | 7/2008 | Schroder |
| 2010/0079152 A1 | 4/2010 | Kim et al. |

* cited by examiner

METHOD FOR CALIBRATING APPARATUSES FOR DETERMINING THE MOISTURE CONTENT OF PRODUCTS BASED ON CAPACITIVE MEASUREMENTS, AND DEVICE FOR STIMULATING THE DIELECTRIC PROPERTIES OF PRODUCTS, SUCH AS WOOD, FOR USE IN THIS METHOD

This invention relates to a method for calibrating apparatuses for determining the moisture content of products, based on capacitive measurements, and a device for simulating the dielectric properties of products, such as wood, for use in this method.

The sector to which this invention mainly relates is the wood working sector, which has the need to determine the moisture content of the wood, based on its dielectric properties. The identification of the moisture content of wood (in particular planks) is essential in order to evaluate its structural properties correctly.

This invention is in any case also intended to be used in other sectors with similar requirements.

Currently, there are many prior art methods for estimating the moisture content of materials by measuring their dielectric properties. Some examples of these methods are described in patents U.S. Pat. Nos. 6,147,503, 6,388,453, 6,784,671 and 7,068,050.

In general, all known methods comprise inserting the piece of wood (or other material), whose moisture content must be calculated, between the first and second plate of a capacitor, in general of the flat type; the application of a first signal to the first plate of the capacitor, using the plate as a transmitting antenna; the detection on the second plate of a second signal induced by the first signal, using the second plate as a receiving antenna. Based on this induced signal, an overall electric value is calculated, and based on the value of the latter, the moisture content is determined.

Nonetheless, all known apparatuses require a preliminary calibration to give a correlation between the values measured and the moisture content.

In particular, every apparatus can be calibrated by measuring a set of samples with it or with an independent system that calculates the water content of the same samples, that in turn must be chosen so as to give a complete view on the type of material (for example pine, fir, oak wood, etc), possible sizes of it (at least at discreet intervals), and moisture content (also in this case, a panoramic view at discreet intervals may be sufficient).

With regards to the independent measurement system, this can be for example, the dry system, which comprises weighing the sample, drying it completely in an oven until the water evaporates completely, and then weighing the sample again; the moisture is then defined as u=(P−Ps)/Ps, where P is the initial weight and Ps is the dry weight.

However, this known method has great disadvantages because it is considerably costly in terms of time (tens or hundreds of measurements may be required for each apparatus) and because it substantially implies the loss of all the samples, which must be dried completely.

To try to simplify this matter, one single calibration has been proposed, for a specific model of measuring apparatus, assuming that the same apparatuses are able to give identical measurements when identical samples are used.

Nonetheless, experience has proven that there are never two identical apparatuses in reality, because the construction tolerances for electronic components and the plates of the capacitor (in addition to small assembly differences), can affect the measurement in a fairly significant way, thus requiring the calibration of each individual apparatus.

In this situation, the technical purposes which forms the basis of this invention is to provide a method for calibrating an apparatus for determining the moisture content of products, based on capacitive measurements, and to provide a device for simulating the dielectric properties of products, such as wood, for use in this method, which overcome the above-mentioned disadvantages.

And in particular, the technical purpose of this invention is to provide a device for simulating the dielectric properties of products, such as wood, which allows simulation of the presence of a product with known characteristics inside the measuring device (such as sizes, type of wood, and moisture content).

An additional technical purpose of this invention is to provide a method for calibrating apparatuses for determining the moisture content of products, based on capacitive measurements which requires a reduced execution time and does not require a complete series of samples for each apparatus to be calibrated, or destruction of the samples of material.

The technical purpose specified and the aims indicated, are substantially achieved with a method for calibrating apparatuses for determining the moisture content of products, based on capacitive measurements, and a device for simulating the dielectric properties of products, such as wood, for use in this method, as described in the appended claims.

Further characteristics and advantages of this invention will be found in the detailed description of some preferred, but not exclusive, embodiments of a device for simulating the dielectric properties of products and a method for calibrating apparatuses for determining the moisture content of products, based on capacitive measurements, described with reference to the accompanying drawings, in which.

Figure 1:
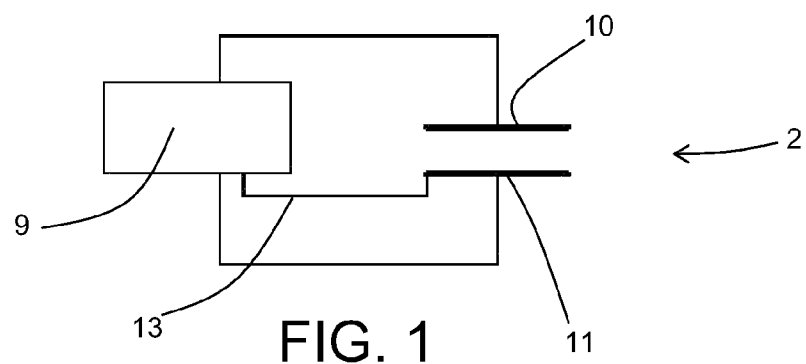
FIG. 1 shows a schematic view of an apparatus for determining the moisture content of products, based on capacitive measurements.

With reference to the accompanying drawings, the numeral 1 denotes as a whole a device for simulating the dielectric properties of products, such as wood, built according to this invention, while the numeral 2 denotes an apparatus 2 for determining the moisture content of products.

The device 1 according to this invention is represented in four possible alternative embodiments, in FIGS. 4 to 7.

In any case, in general, it comprises at least a first receiving antenna 3, at least an electric connection terminal 4, and at least an adjustable impedance 5, electrically connected between the first antenna 3 and the electric terminal 4.

Figure 6:
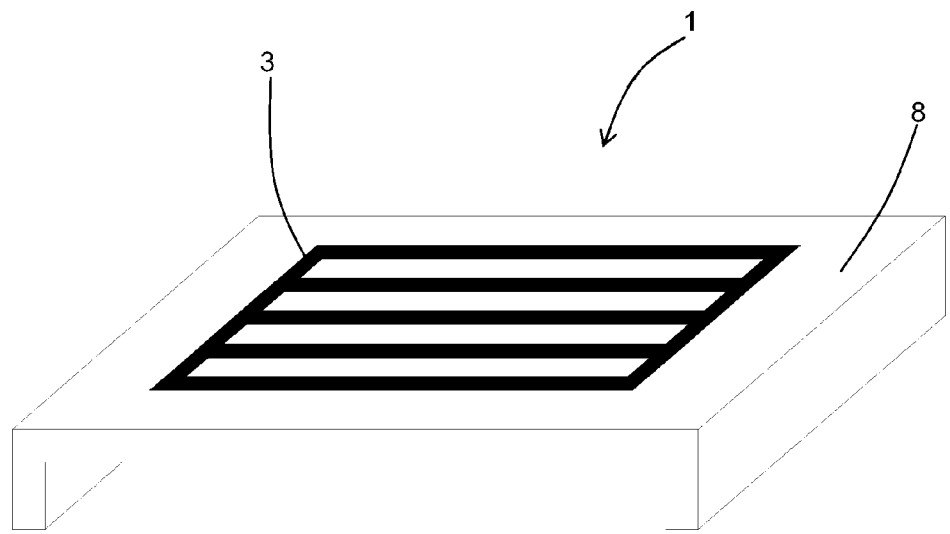
FIG. 6 shows an axonometric view of a third embodiment of a detail of a simulation device built according to this invention.
Figure 7:
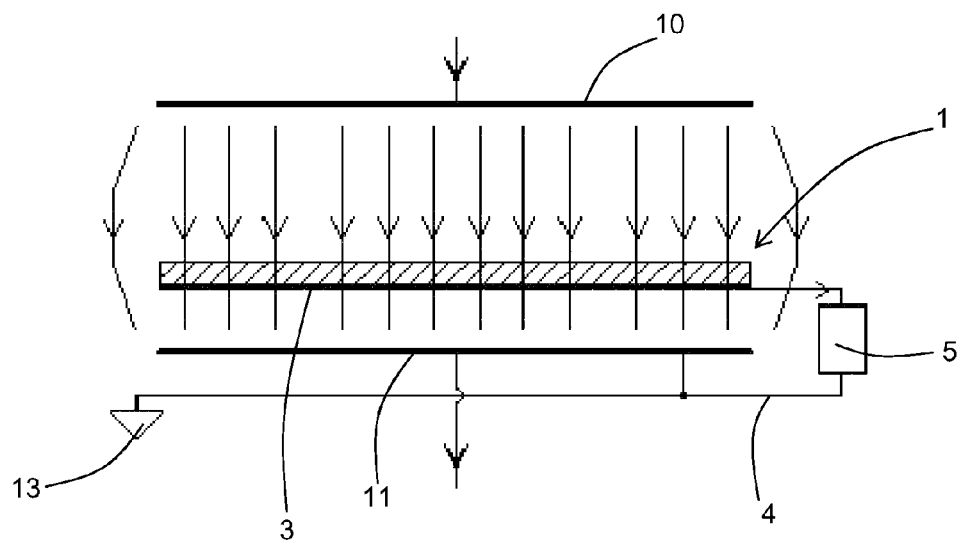
FIG. 7 shows a detail of FIG. 2 with a simulation device built according to this invention, schematically introduced inside the apparatus.

With regards to the first receiving antenna 3, this can be constituted by a flat plate or by a conductive grid (as in FIG. 6).

In the preferred embodiment, the adjustable impedance 5 comprises at least one resistor 6 and at least one capacitor 7, at least one of them adjustable. In particular, in the embodiment shown, the resistor 6 and the capacitor 7 are connected in series, and while the capacitor 7 has a fixed capacitance value, the resistor 6 has a variable resistance 6 value. With regards to the values of these components, these must be chosen empirically, according to the methods described below, so that the electro-magnetic behaviour of device 1 reflects the dielectric behaviour of the piece of material to be simulated.

Figure 5:
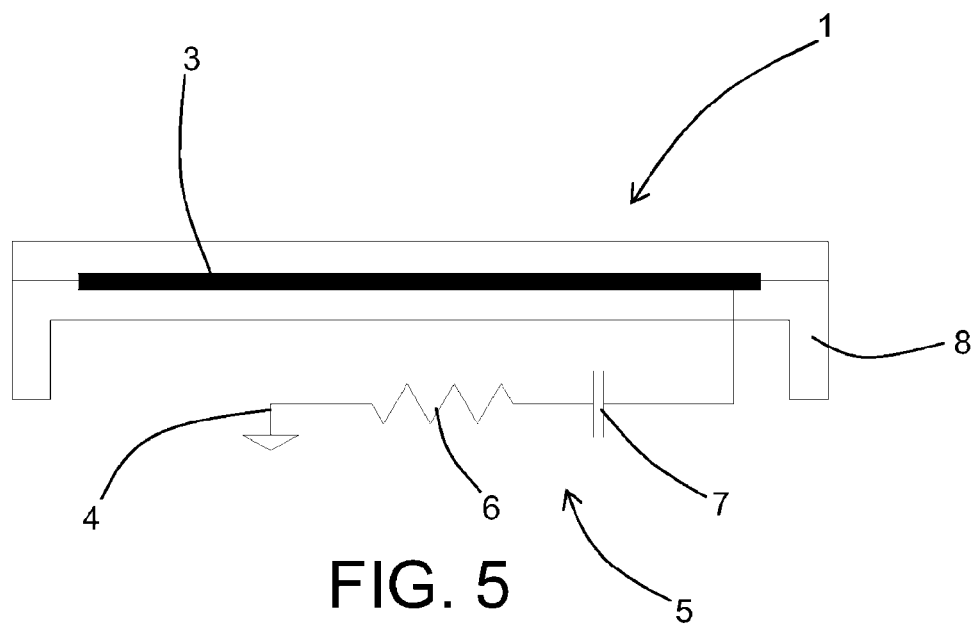
FIG. 5 shows a schematic lateral view of a second embodiment of a simulation device built according to this invention.

The electric terminal 4 can be electrically connected to an apparatus 2 or to another circuit external to the device 1. As explained below, in the preferred embodiment of this invention, the electric terminal 4 can be connected to the earth 13 of an apparatus 2 for determining the moisture content of products, through capacitive measurements. Advantageously, to ensure the protection of the first receiving antenna 3, and its correct positioning, the calibration device 1 also comprises a support structure 8 which supports the first antenna 3. In particular, as shown the accompanying drawings, the first antenna 3 can be located on a surface external to the support structure 8 (FIGS. 4, 6, and 7) or be inserted in it (FIG. 5).

As mentioned, in order for the device 1 according to this invention to simulate the presence of a product, such as a piece of wood, once located within the two plates of an apparatus 2 for determining the moisture content of products based on capacitive measurements, and if necessary connected to the electric circuit of this apparatus 2 (and in particular its earth 13), its impedance 5 must be set properly.

This result can be easily obtained with empirical tests.

The starting step of these tests is to have available a measuring apparatus 2 (the type is described in detail below), already calibrated, for which the readings corresponding to the different types of material are known.

At this point, it is sufficient to insert the device 1 in the apparatus 2 and take the measurements (according to what is described below), gradually changing the impedance 5 of the device 1, until a correspondence is found between what is measured with the device 1 and a point of the possible series of measurements obtained with the apparatus 2 for an actual product.

For example, in case of the device 1 shown in the accompanying drawings, two values R1 and C1 can be found (resistance 6 and capacitance, respectively), such that the reading obtained with the apparatus 2 corresponds to the reading that can be obtained by inserting in the same apparatus 2 a sample of pine wood of width X1 and height Z1, with a moisture content U1.

Similarly, two values R2, C2 can be found, that will give the same reading as a sample of pine wood of width X2 and height Z2, with moisture content U2.

Note also that several samples with different characteristics (for example different material and different moisture content) can correspond to the same reading of the reference apparatus 2. In any case, in practice, this cannot represent an uncertainty for the use of apparatuses, since the type of material and sizes of the sample are always known beforehand, the only unknown value is the moisture content.

The development step takes place differently but only in part, in case device 1 is made with one single variable component (resistor 6 or capacitor 7). In this case, the first tests will have the purpose to determine the optimal value for the capacitance 7 or resistance 6, able to "centre" all the measurements in relation to the area in which the actual ones fall (in particular with reference to the measuring system that uses complex values, described below), while the following tests will have the purpose of finding the resistance 6 or capacitance 7 values respectively, able to move the measurements inside this area. With regard to the calibration method for apparatuses for determining the moisture content of products based on capacitive measurements, according to this invention, this is mainly characterised by the fact that the device 1 described herein is used for simulating the presence of a plurality of different products (in terms of type and/or size and/or moisture content) in the apparatus 2, without the need to use actual products.

An apparatus 2 of this type is schematically shown in FIG. 1. It consists of an electronic system 9 that feeds a transmitting antenna 10 (constituted by a first plate of a flat capacitor), with a voltage signal. This signal induces a current signal in a second receiving antenna 11, connected in turn to the electronic system 9, able therefore to determine the moisture content, based on the detected signal induced (according to known methods).

Figure 2:
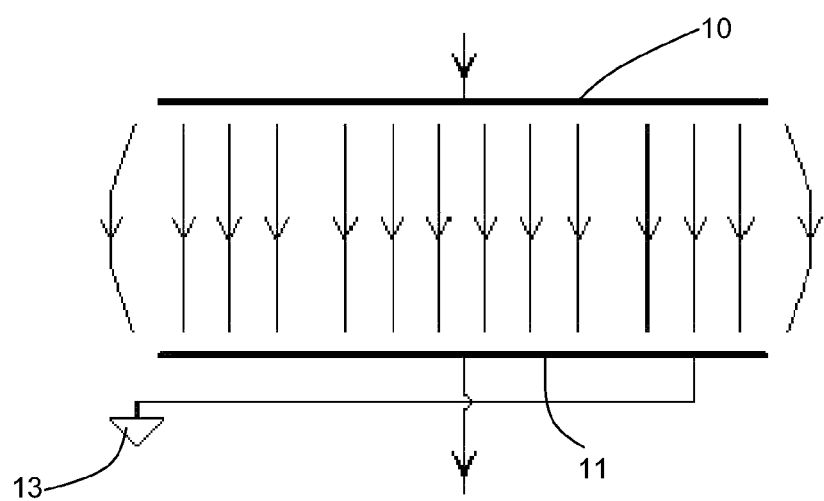
FIG. 2 shows a detail of the apparatus of FIG. 1, in the absence of products.
Figure 3:
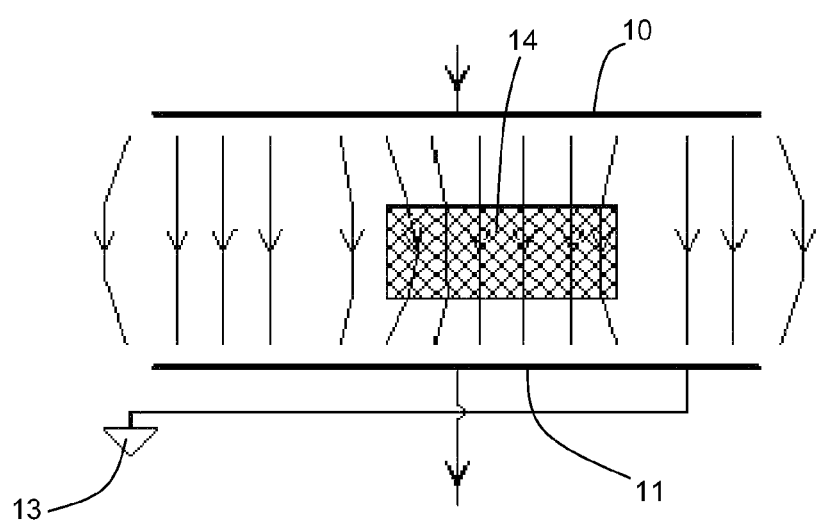
FIG. 3 shows a detail of FIG. 2 with a product to be measured, introduced inside the apparatus.
Figure 4:
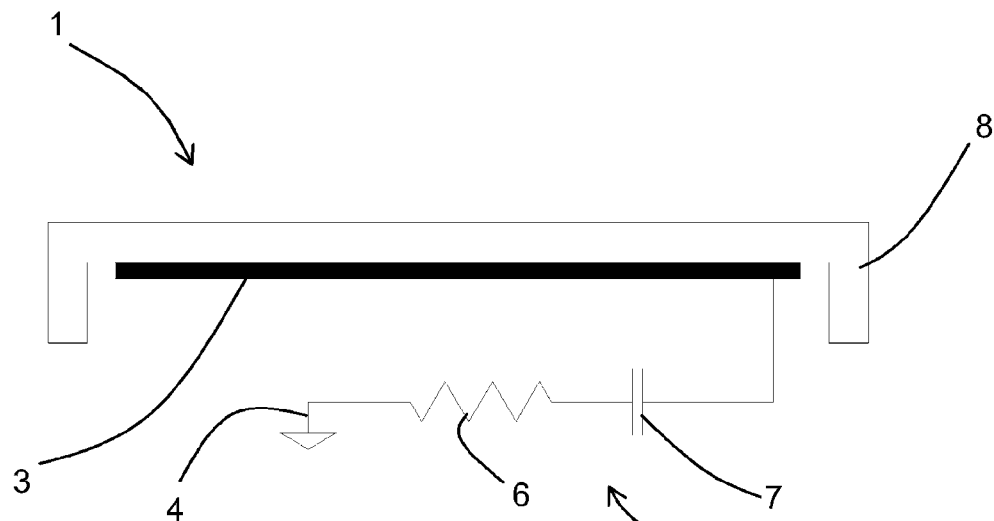
FIG. 4 shows a schematic lateral view of a first embodiment of a simulation device built according to this invention.

FIGS. 2 and 3 show a detail of the measuring area of this apparatus 2 (the area between the plates), in the absence of products and with a piece of wood 14 inserted in it, respectively. The trend of the electro-magnetic field is also shown in these figures, which is generated in the work area.

The calibration method according to this invention comprises first inserting a device 1 of the above described type in the measuring area of the apparatus 2 to be calibrated, and setting the relative impedance 5 to a first pre-established value. Advantageously, the electric terminal 4 of device 1 is connected either to the electric circuit of the same apparatus 2 or simply to its earth 13.

At this point, the method comprises the execution, with the apparatus 2, of a first capacitive measurement with the device 1 inserted in the measuring area and with impedance 5, set to a first predetermined value.

In particular, in the embodiment described, the electronic system 9 of the apparatus 2 applies a known voltage signal to the transmitting antenna 10 and determines the current induced in the second receiving antenna 11. It must be noticed that, according to operating needs, each measurement can correspond directly to the induced current or to an electric value derived from it (such as a voltage, an impedance value 5, an impedance 5 variation, etc.). In any case, advantageously, each measurement is recorded and processed as an overall value (storing indifferently either the modulus and the phase or the actual part and the imaginary one).

Once the first measurement is taken, the method comprises modifying the impedance value 5 at least once, to a different predetermined value, and taking the capacitive measurement again, for each different impedance value 5 set. The relative representative overall value is stored for each measurement.

Figure 8:
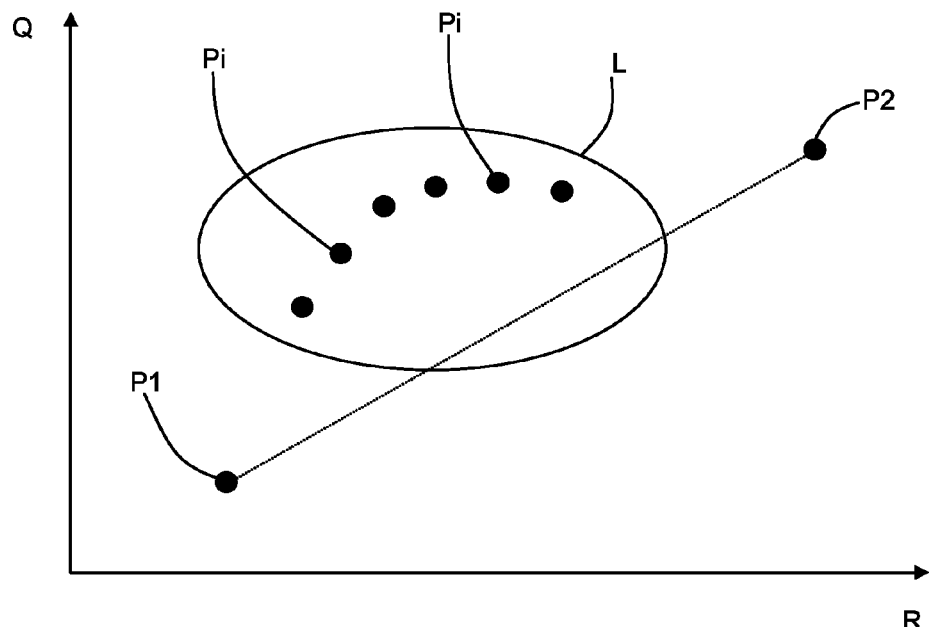
FIG. 8 shows the projection in the complex plane, of a plurality of points representing capacitive measurements taken with an apparatus for determining the moisture content to be calibrated.

FIG. 8 shows the complex plane (actual coordinates R and imaginary coordinates Q) which represents some points obtained with the apparatus 2 to be calibrated. In particular, two limit points are shown, connected by a segment, which represent a measurement taken in the absence of the device 1 P1, and a measurement taken in the absence of signal applied to the transmitting plate P2, respectively. In addition, a closed line L (elliptical) is shown, which delimits the area of the complex plane, in which all the measurements Pi, taken with the different impedance values 5 of device 1, fall.

The following step of the calibration method comprises comparing each capacitive measurement taken with this method, with a corresponding known reference capacitive measurement (P10, P20, Pi0).

In the preferred embodiment, the known reference capacitive measurements are measurements that were previously obtained with a calibrated reference apparatus 2, with the same impedance value 5 as the simulation device 1. In other words, since each value of the simulation device 1 is represented by one (or more) actual product, the known reference measurement is the one that should be obtained with an apparatus 2 calibrated for that actual product.

Figure 9:
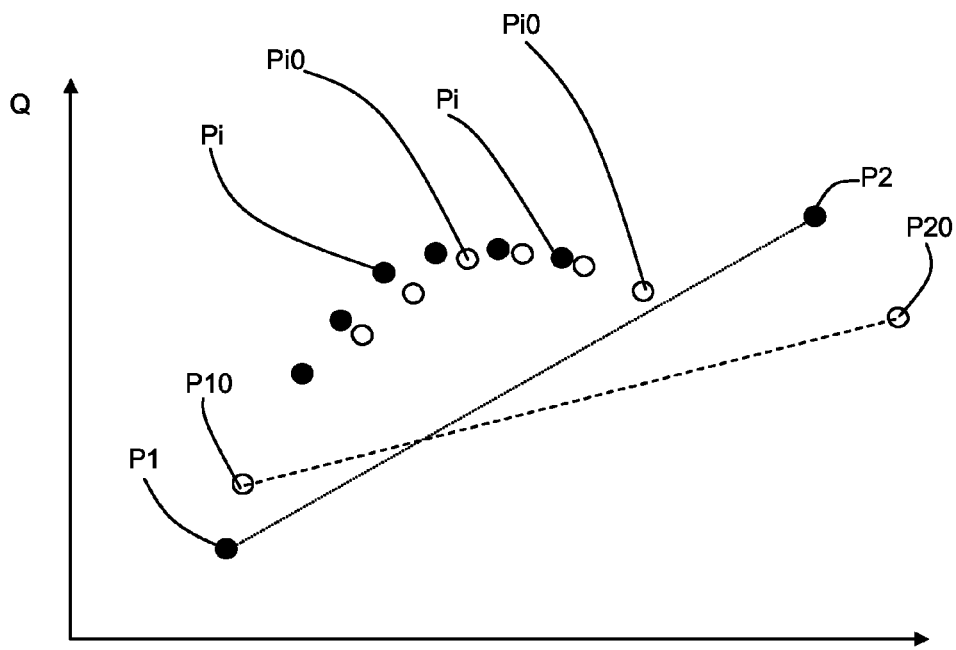
FIG. 9 shows the position in the complex plane, of the points represented in FIG. 8 in relation to that of known, reference capacitive measurements, taken with a reference apparatus previously calibrated.

This comparison step is shown in FIG. 9, which represents in the complex plane (R, Q), the points obtained with all the measurements taken with the apparatus 2 to be calibrated (black dots P1, P2, Pi), and the corresponding points relative to the known reference measurements (light dots P10, P20, Pi0).

The last step of the method according to this invention is the step of actually calibrating the apparatus 2 on the basis of the result of the comparison step.

In particular, in the embodiment described herein, the calibration step comprises determining one or more transformation formula in the complex plane, to apply to the measurements taken with the apparatus 2 to be calibrated. These transformation formulas are determined so that the measurements taken with the apparatus 2 to be calibrated coincide with the known reference measurements in the complex plane. In the case shown in FIG. 9, in particular, the formulas needed to associate the points measured with the reference points are rototranslation formulas. Nonetheless, in other cases, these formulas can be different, for example, they might comprise a scale factor along one or both reference axes of the complex plane.

Finally, it must be noticed that the formulas can be applied to modify the readings of the machine so as to generate fictitious formulas to which the algorithms for calculating the moisture content will be applied, and to modify the same algorithms to make them suitable for operating directly on the measurements obtained by the machine.

As mentioned, even two hypothetically identical apparatuses do not give the same reading. Therefore, if one of the two is considered to be the reference apparatus 2 and calibrated it in a traditional way, it is possible to identify the algorithm able to give the moisture content, given the type of material, its dimensions and the measurement obtained. Since the same moisture values can be obtained also with the other apparatus 2, starting from different measurements, the transformation formulas have the purpose of bringing the second apparatus 2 to the same operating condition as the first, for which the correspondence between the reading and the moisture is known.

The method according to this invention is implemented based on what has been described so far.

The starting point is to have available a reference apparatus 2 for measuring the moisture content, which is already calibrated, so that the measurements obtained with it represent specific products with known dimensions, properties (material) and moisture.

The following step, for calibrating other measuring apparatuses, is to produce a device 1 of the above described type, and perfect it, by identifying a plurality of values for setting the respective impedance 5, such that the measurements taken by inserting the device 1 in the reference apparatus 2 for each of said values, represent a plurality of actual measurements, that can be obtained with the same apparatus 2, and therefore a plurality of different products.

At this point, it is possible to proceed with the calibration of a new apparatus 2, by simply inserting the device 1 in the work area, setting the respective impedance 5, in line with at least part of the previously established settings, and taking the respective measurements.

By comparing these measurements with the reference ones, it is possible to determine the transformation to apply (directly or indirectly) to the measurements of the apparatus 2 to be calibrated, so that these can be effectively used to calculate the moisture content of the products examined.

Note that it is always preferable to perform a large number of simulations in order to avoid possible measurement errors and to identify complex transformation formulas.

This invention has important advantages.

First of all, thanks to this invention, it is possible, at least for each type of apparatus 2 for measuring the moisture content, to proceed with a single calibration based on prior art methods, such as the dry system, and to create, based on this calibration, a device able to reproduce the dielectric behaviour of a plurality of different products.

To calibrate all subsequent apparatuses of that type, it is sufficient to use the device as simulator of the presence of products and bring the measurements taken by the individual apparatuses into line with those of the reference apparatus 2.

Consequently, the calibration method according to this invention (for the second apparatus 2 and subsequent ones) is first a method that requires a significantly reduced execution time compared with conventional methods:

Second, it does not require a complete series of samples of materials, nor the destruction of any sample.

Moreover, this method can be repeated with extreme accuracy, since each device of the above described type, once perfected, is able to always simulate the dielectric properties of the reference products in the same way.

It should also be noticed that this invention is fairly easy to produce and the cost of implementing the invention is not very high.

The invention described above may be modified and adapted in several ways without thereby departing from the scope of the inventive concept. All the details may be substituted by other technically equivalent details and in practice, all the materials used, shapes and sizes of the various components, may vary according to requirements.

The invention claimed is:

1. A calibrating device for use with an apparatus (2) effective for determining the moisture content of products, including wood, the apparatus (2) having a transmitting antenna and a second receiving antenna which are electrically connected to each other and a measuring zone which is located between the transmitting antenna and the second receiving antenna and wherein a product whose moisture content is to be determined can be positioned between the transmitting antenna and the second receiving antenna, the calibrating device comprising:

a first receiving antenna (3) which is shaped so that it can be inserted in and removed from the measuring zone of the apparatus (2) to be calibrated;

an electric terminal (4) which is configured so that, in operation, it can be electrically connected to the apparatus (2) or to another item; and an adjustable impedance (5), electrically connected, via one or more electric conductors, between the first antenna (3) and the electric terminal (4), the impedance (5) being adjustable such that the calibrating device can effectively simulate the dielectric properties of a plurality of products having different moisture contents when the calibrating device is inserted in the measuring zone of the apparatus.

2. The calibrating device according to claim 1, characterised in that the impedance (5) comprises at least one resistor (6) and at least one capacitor (7), at least one of which is adjustable.

3. The calibrating device according to claim 2, characterised in that the resistor (6) and the capacitor (7) are connected in series.

4. The calibrating device according to claim 2, characterised in that the capacitor (7) has a fixed capacitance value, and also being characterised in that the resistor (6) has an adjustable resistance value.

5. The calibrating device according to claim 1, characterised in that the device also comprises a supporting structure (8) supporting the first antenna (3).

6. The calibrating device according to claim 5, characterised in that the first antenna (3) is positioned on an outer surface of the supporting structure (8) or is inserted in it.

7. A calibrating method for apparatuses for determining the moisture content of products based on capacitive measurements, characterised in that it comprises the operating steps of:
inserting in a measuring zone of an apparatus (2) to be calibrated, a first receiving antenna (3) of a calibrating device (1) made in accordance with claim 1,
setting the impedance (5) to a predetermined value;
using the apparatus (2) to take a capacitive measurement with the device (1) inserted in the measuring zone;
modifying at least once the value of the impedance (5) to a different predetermined value and repeating the capacitive measurement for each different impedance (5) value;
comparing each capacitive measurement taken in this way with a corresponding known reference capacitive measurement;
calibrating the apparatus (2) based on that comparison.

8. The method according to claim 7, characterised in that it also comprises, before the steps of taking the measurement, the step of connecting the device (1) electric terminal (4) to the apparatus (2).

9. The method according to claim 7, characterised in that it also comprises, before the steps of taking the measurement, the step of connecting the device (1) electric terminal (4) to earth.

10. The method according to claim 7, characterised in that the steps of taking the capacitive measurements involve applying a known voltage to a transmitting antenna (10) of the apparatus (2) and detecting the current induced in a second, receiving antenna (11) of the apparatus (2), each measurement corresponding either to the induced current or to an electric quantity derived from it.

11. The method according to claim 10, characterised in that each measurement is saved and processed as a complex quantity.

12. The method according to claim 11, characterised in that the comparison step involves a comparison in the complex plane between the measurements taken and the known reference measurements.

13. The method according to claim 12, characterised in that the calibrating step involves the identification of one or more formulae for transformation in the complex plane of the measurements taken with the apparatus (2) to be calibrated, the transformation formulae being identified in such a way that in the complex plane the measurements taken with the apparatus (2) to be calibrated are made to coincide with the known reference measurements.

14. The method according to claim 7, characterised in that the known reference measurements are obtained by means of an advance measuring step carried out by inserting the device (1) in a reference apparatus (2) and setting the relative impedance (5) to the predetermined values.

15. The method according to claim 14, characterised in that it also comprises the operating step of associating the known reference measurements with products which have known dimensions, properties and moisture.

16. The calibrating device of claim 1, wherein the impedance (5) comprises a resistor (6) and a capacitor (7), the resistor (6) and the capacitor (7) being connected in series, and the resistor (6) having an adjustable resistance value.

* * * * *